(12) United States Patent
Hoang et al.

(10) Patent No.: US 9,480,833 B2
(45) Date of Patent: Nov. 1, 2016

(54) ANTIMICROBIAL IV ACCESS CAP

(75) Inventors: Minh Quang Hoang, Sandy, UT (US); Jonathan Karl Burkholz, Salt Lake City, UT (US); Kelly David Christensen, Centerville, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 13/180,995

(22) Filed: Jul. 12, 2011

(65) Prior Publication Data

US 2012/0016318 A1    Jan. 19, 2012

Related U.S. Application Data

(60) Provisional application No. 61/364,447, filed on Jul. 15, 2010.

(51) Int. Cl.
*A61M 39/16* (2006.01)
*A61M 39/20* (2006.01)
*A61M 39/02* (2006.01)

(52) U.S. Cl.
CPC .......... *A61M 39/16* (2013.01); *A61M 39/165* (2013.01); *A61M 39/20* (2013.01); *A61M 2039/0285* (2013.01)

(58) Field of Classification Search
CPC ............. A61M 39/20; A61M 39/162; A61M 2039/0285; A61M 39/16; A61M 39/165
USPC ........... 604/288.01, 533, 905, 29, 283, 256, 604/403; 427/2.1, 2.3
See application file for complete search history.

(56) References Cited

U.S. PATENT DOCUMENTS

| | | | |
|---|---|---|---|
| 2,961,682 A | | 11/1960 | Wurmbock et al. |
| 4,280,632 A | | 7/1981 | Yuhara |
| 4,282,891 A | | 8/1981 | Duceppe |
| 4,354,490 A | | 10/1982 | Rogers |
| 4,417,890 A | * | 11/1983 | Dennehey et al. ........... 604/256 |
| 4,432,764 A | | 2/1984 | Lopez |
| 4,440,207 A | * | 4/1984 | Genatempo et al. ......... 150/154 |
| 4,444,310 A | | 4/1984 | Odell |
| 4,584,192 A | | 4/1986 | Dell et al. |
| 4,624,664 A | | 11/1986 | Peluso et al. |
| 4,626,664 A | | 12/1986 | Grise |

(Continued)

FOREIGN PATENT DOCUMENTS

| | | |
|---|---|---|
| EP | 1 649 890 A1 | 4/2006 |
| EP | 2 606 930 A1 | 6/2013 |

(Continued)

OTHER PUBLICATIONS

"Corrected Petition for Inter Partes Review Under 35 U.S.C. §§ 311-319 and 37 C.F.R. § 42,100 et seq.," USPTO, Patent Trial and Appeal Board, *Excelsior Medical Corporation v. Becton, Dickinson and Company*, Case IPR2014-00880, U.S. Pat. No. 8,740,864, pp. 1-48, Jun. 23, 2014.

(Continued)

*Primary Examiner* — Bhisma Mehta
*Assistant Examiner* — Brandy S Lee
(74) *Attorney, Agent, or Firm* — Jeanne Lukasavage; Craig Metcalf; Kirton McConkie

(57) ABSTRACT

An antimicrobial IV access cap having an inner surface for retaining an antimicrobial agent, and further configured to receive a portion of an access port of an intravascular device.

12 Claims, 18 Drawing Sheets

(56) References Cited

U.S. PATENT DOCUMENTS

| | | | |
|---|---|---|---|
| 4,655,762 A | 4/1987 | Rogers | |
| 4,671,306 A | 6/1987 | Spector | |
| 4,716,032 A | 12/1987 | Westfall et al. | |
| 4,753,358 A * | 6/1988 | Virca | B01L 3/50825 215/230 |
| 4,778,447 A | 10/1988 | Velde et al. | |
| 4,915,934 A | 4/1990 | Tomlinson | |
| 4,925,668 A | 5/1990 | Khan et al. | |
| 4,989,733 A | 2/1991 | Patry | |
| 4,991,629 A | 2/1991 | Ernesto et al. | |
| 5,023,082 A | 6/1991 | Friedman et al. | |
| 5,195,957 A | 3/1993 | Tollini | |
| 5,242,425 A | 9/1993 | White et al. | |
| 5,334,388 A | 8/1994 | Hoang et al. | |
| 5,335,373 A | 8/1994 | Dresdner et al. | |
| 5,512,199 A | 4/1996 | Khan et al. | |
| 5,547,662 A | 8/1996 | Khan et al. | |
| 5,554,106 A | 9/1996 | Layman-Spillar et al. | |
| 5,554,135 A * | 9/1996 | Menyhay | 604/256 |
| 5,569,207 A | 10/1996 | Gisselberg et al. | |
| 5,616,338 A | 4/1997 | Fox, Jr. et al. | |
| 5,620,424 A * | 4/1997 | Abramson | 604/265 |
| 5,639,310 A | 6/1997 | Giampaolo, Jr. | |
| 5,641,464 A | 6/1997 | Briggs, III et al. | |
| 5,686,096 A | 11/1997 | Khan et al. | |
| 5,694,978 A | 12/1997 | Heilmann et al. | |
| 5,702,017 A | 12/1997 | Goncalves | |
| 5,706,944 A | 1/1998 | Hoang et al. | |
| 5,722,537 A | 3/1998 | Sigler | |
| 5,743,884 A | 4/1998 | Hasson et al. | |
| 5,792,120 A | 8/1998 | Menyhay | |
| 5,817,344 A | 10/1998 | Hoang et al. | |
| 5,861,440 A | 1/1999 | Gohla et al. | |
| 5,954,957 A | 9/1999 | Chin-Loy et al. | |
| 5,989,229 A | 11/1999 | Chiappetta | |
| 6,045,539 A | 4/2000 | Menyhay | |
| 6,051,609 A | 4/2000 | Yu et al. | |
| 6,116,468 A | 9/2000 | Nilson | |
| 6,117,114 A | 9/2000 | Paradis | |
| 6,196,998 B1 | 3/2001 | Jansen et al. | |
| 6,227,391 B1 | 5/2001 | King | |
| 6,337,357 B1 | 1/2002 | Fukunishi et al. | |
| 6,413,539 B1 | 7/2002 | Shalaby | |
| 6,488,942 B1 | 12/2002 | Ingemann | |
| 6,523,686 B1 | 2/2003 | Bae | |
| RE38,145 E | 6/2003 | Lynn | |
| 6,708,363 B2 | 3/2004 | Larsen | |
| 6,846,846 B2 | 1/2005 | Modak et al. | |
| 6,861,060 B1 | 3/2005 | Luriya et al. | |
| 6,911,025 B2 | 6/2005 | Miyahara | |
| 6,994,315 B2 | 2/2006 | Ryan et al. | |
| 7,083,605 B2 | 8/2006 | Miyahara | |
| 7,198,611 B2 | 4/2007 | Connell et al. | |
| 7,198,800 B1 | 4/2007 | Ko | |
| 7,268,165 B2 | 9/2007 | Greten et al. | |
| 7,282,186 B2 | 10/2007 | Lake, Jr. et al. | |
| 7,452,349 B2 | 11/2008 | Miyahara | |
| 7,682,561 B2 | 3/2010 | Davis et al. | |
| 7,704,935 B1 | 4/2010 | Davis et al. | |
| 7,763,006 B2 | 7/2010 | Tennican | |
| 7,828,186 B2 | 11/2010 | Wales | |
| 7,922,701 B2 | 4/2011 | Buchman | |
| 8,065,773 B2 | 11/2011 | Vaillancourt et al. | |
| 8,113,731 B2 | 2/2012 | Cable, Jr. et al. | |
| 8,162,899 B2 | 4/2012 | Tennican | |
| 8,167,847 B2 | 5/2012 | Anderson et al. | |
| 8,491,546 B2 | 7/2013 | Hoang et al. | |
| 2001/0016589 A1 | 8/2001 | Modak et al. | |
| 2002/0144705 A1 | 10/2002 | Brattesani et al. | |
| 2003/0072781 A1 | 4/2003 | Pelerin | |
| 2003/0109853 A1 | 6/2003 | Harding et al. | |
| 2003/0153865 A1 | 8/2003 | Connell et al. | |
| 2003/0162839 A1 | 8/2003 | Symington et al. | |
| 2004/0004019 A1 | 1/2004 | Busch | |
| 2004/0039349 A1 | 2/2004 | Modak et al. | |
| 2004/0258560 A1 | 12/2004 | Lake, Jr. et al. | |
| 2005/0124970 A1 | 6/2005 | Kunin et al. | |
| 2005/0147524 A1 | 7/2005 | Bousquet | |
| 2005/0147525 A1 | 7/2005 | Bousquet | |
| 2005/0222542 A1 | 10/2005 | Burkholz et al. | |
| 2006/0030827 A1 | 2/2006 | Raulerson et al. | |
| 2006/0165751 A1 | 7/2006 | Chudzik et al. | |
| 2006/0239954 A1 | 10/2006 | Sancho | |
| 2007/0112333 A1 | 5/2007 | Hoang et al. | |
| 2007/0202177 A1 | 8/2007 | Hoang | |
| 2007/0225660 A1 | 9/2007 | Lynn | |
| 2007/0282280 A1 | 12/2007 | Tennican | |
| 2008/0019889 A1 | 1/2008 | Rogers et al. | |
| 2008/0027399 A1 | 1/2008 | Harding et al. | |
| 2008/0033371 A1 * | 2/2008 | Updegraff et al. | 604/263 |
| 2008/0075761 A1 | 3/2008 | Modak et al. | |
| 2008/0095680 A1 * | 4/2008 | Steffens et al. | 422/300 |
| 2008/0147047 A1 | 6/2008 | Davis et al. | |
| 2008/0177250 A1 | 7/2008 | Howlett et al. | |
| 2008/0182921 A1 | 7/2008 | Suh et al. | |
| 2009/0008393 A1 | 1/2009 | Howlett et al. | |
| 2009/0028750 A1 | 1/2009 | Ryan | |
| 2009/0028756 A1 | 1/2009 | Shahriari | |
| 2009/0062766 A1 | 3/2009 | Howlett et al. | |
| 2009/0149818 A1 | 6/2009 | Timm | |
| 2009/0149819 A1 | 6/2009 | Chelak | |
| 2009/0175759 A1 | 7/2009 | Davis et al. | |
| 2010/0000040 A1 | 1/2010 | Shaw et al. | |
| 2010/0047123 A1 | 2/2010 | Solomon et al. | |
| 2010/0049170 A1 | 2/2010 | Solomon et al. | |
| 2010/0050351 A1 | 3/2010 | Colantonio et al. | |
| 2010/0172794 A1 | 7/2010 | Ferlic et al. | |
| 2010/0204648 A1 | 8/2010 | Stout et al. | |
| 2010/0292673 A1 * | 11/2010 | Korogi et al. | 604/533 |
| 2011/0150958 A1 | 6/2011 | Davis et al. | |
| 2011/0290799 A1 | 12/2011 | Anderson et al. | |
| 2012/0016318 A1 | 1/2012 | Hoang et al. | |
| 2012/0039765 A1 | 2/2012 | Solomon et al. | |
| 2012/0216360 A1 | 8/2012 | Rogers et al. | |
| 2012/0283693 A1 | 11/2012 | Anderson et al. | |

FOREIGN PATENT DOCUMENTS

| | | |
|---|---|---|
| JP | 2001-258713 A | 9/2001 |
| WO | WO 87/00441 | 1/1987 |
| WO | WO 99/29173 | 6/1999 |
| WO | WO 2006/019782 A2 | 2/2006 |
| WO | 2007/044760 A2 | 4/2007 |
| WO | 2007/137056 A2 | 11/2007 |
| WO | WO 2008/157092 A1 | 12/2008 |
| WO | WO 2010/039171 A1 | 4/2010 |
| WO | 2010/143693 A1 | 12/2010 |
| WO | 2011/053924 A1 | 5/2011 |
| WO | 2011/066586 A1 | 6/2011 |

OTHER PUBLICATIONS

"Patent Owner's Preliminary Response Under 37 C.F.R. § 42,10," USPTO, Patent Trial and Appeal Board, *Excelsior Vledical Corporation v. Becton, Dickinson and Company*, Case IPR2014-00880, U.S. Pat. No. 8,740,864, pp. 1-30, Sep. 16, 2014.

"Decision, Institution of Inter Partes Review, 37 C.F.R. § 42,108," USPTO, Patent Trial and Appeal Board, *Excelsior Vledical Corporation v. Becton, Dickinson and Company*, Case IPR2014-00880, U.S. Pat. No. 8,740,864, pp. 1-21, Nov. 25, 2014.

* cited by examiner

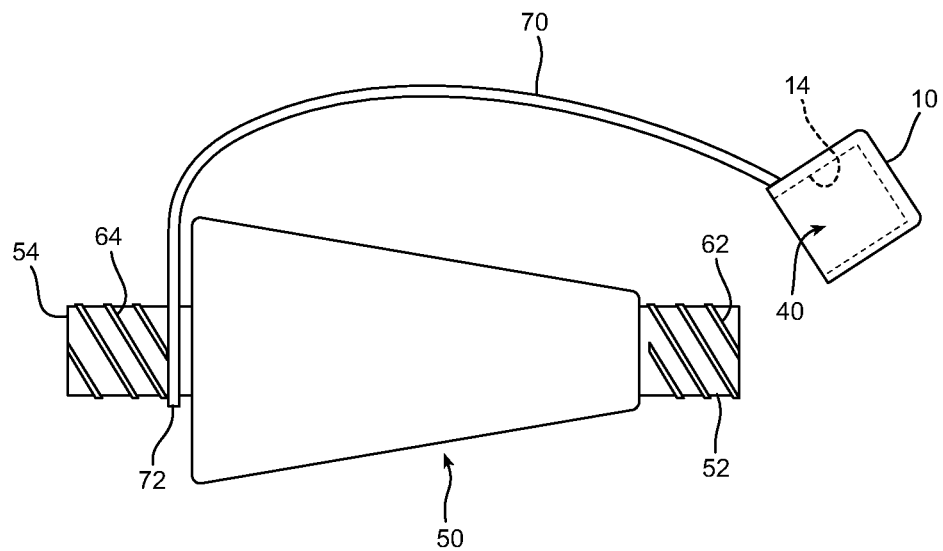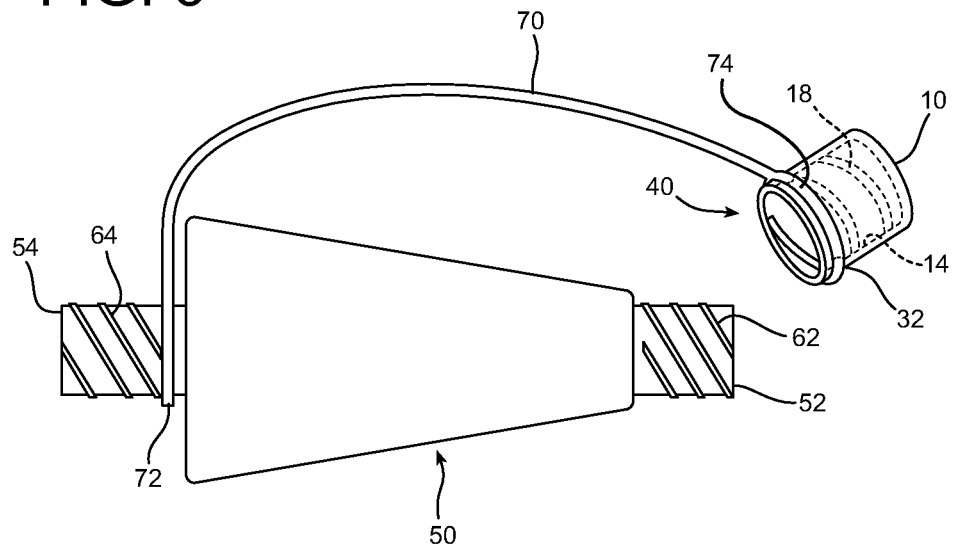

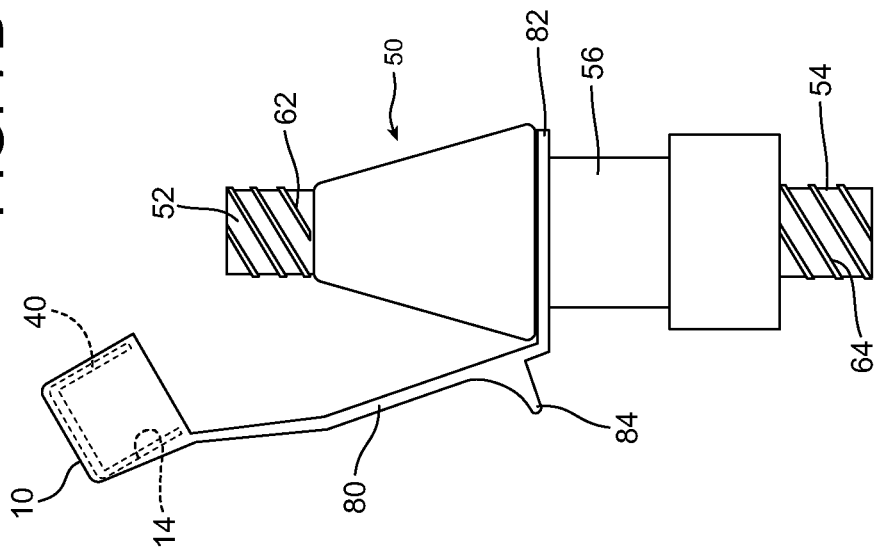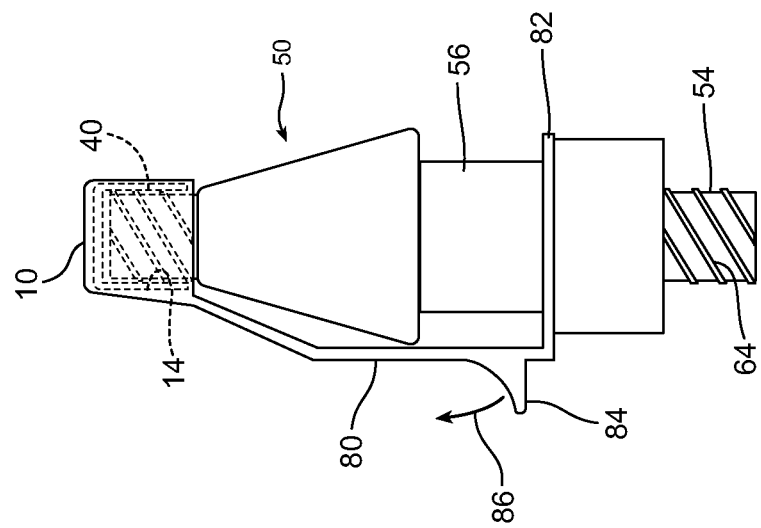

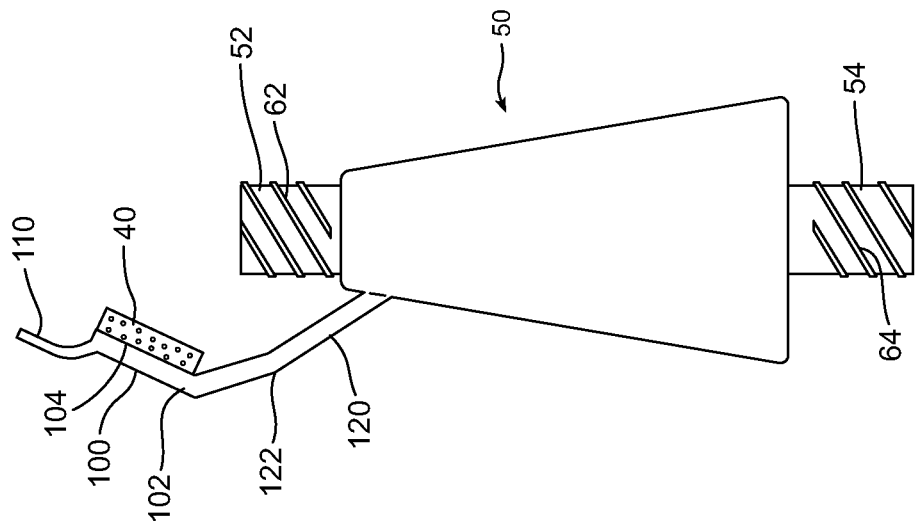
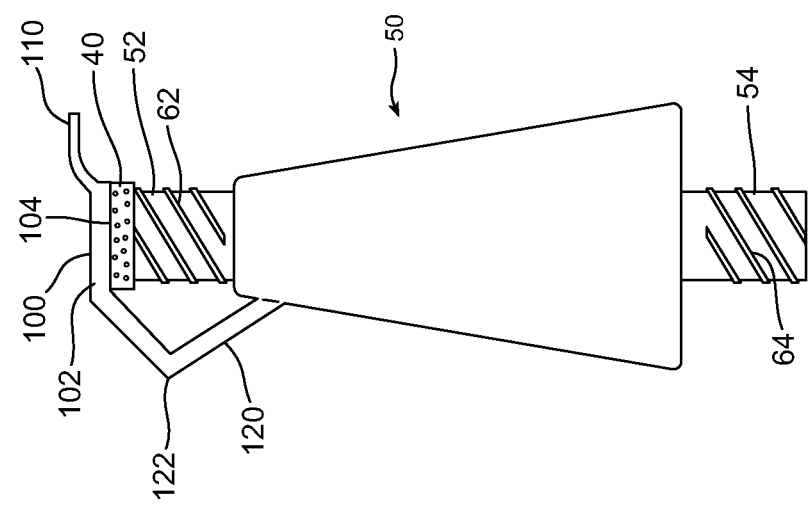

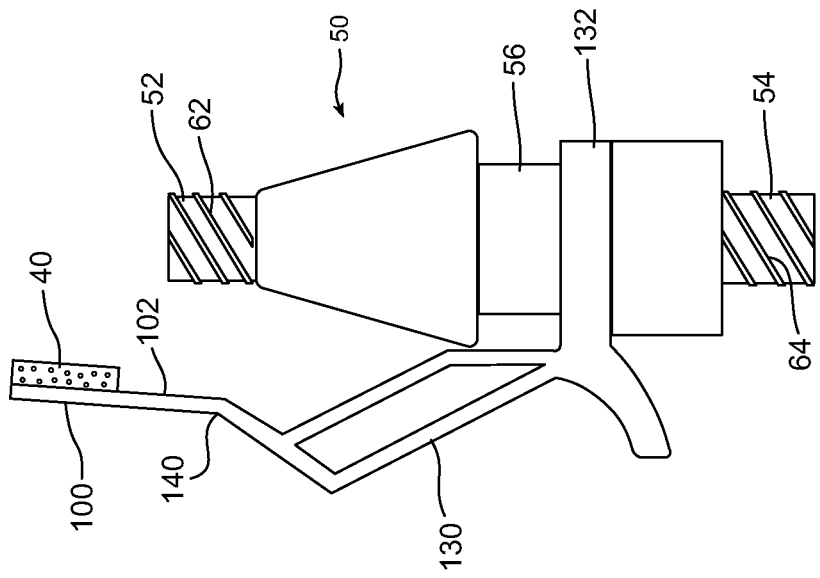
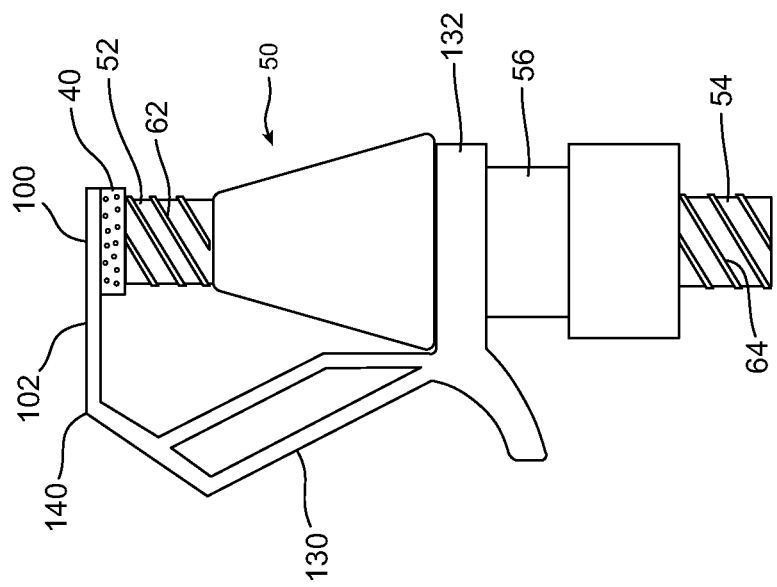

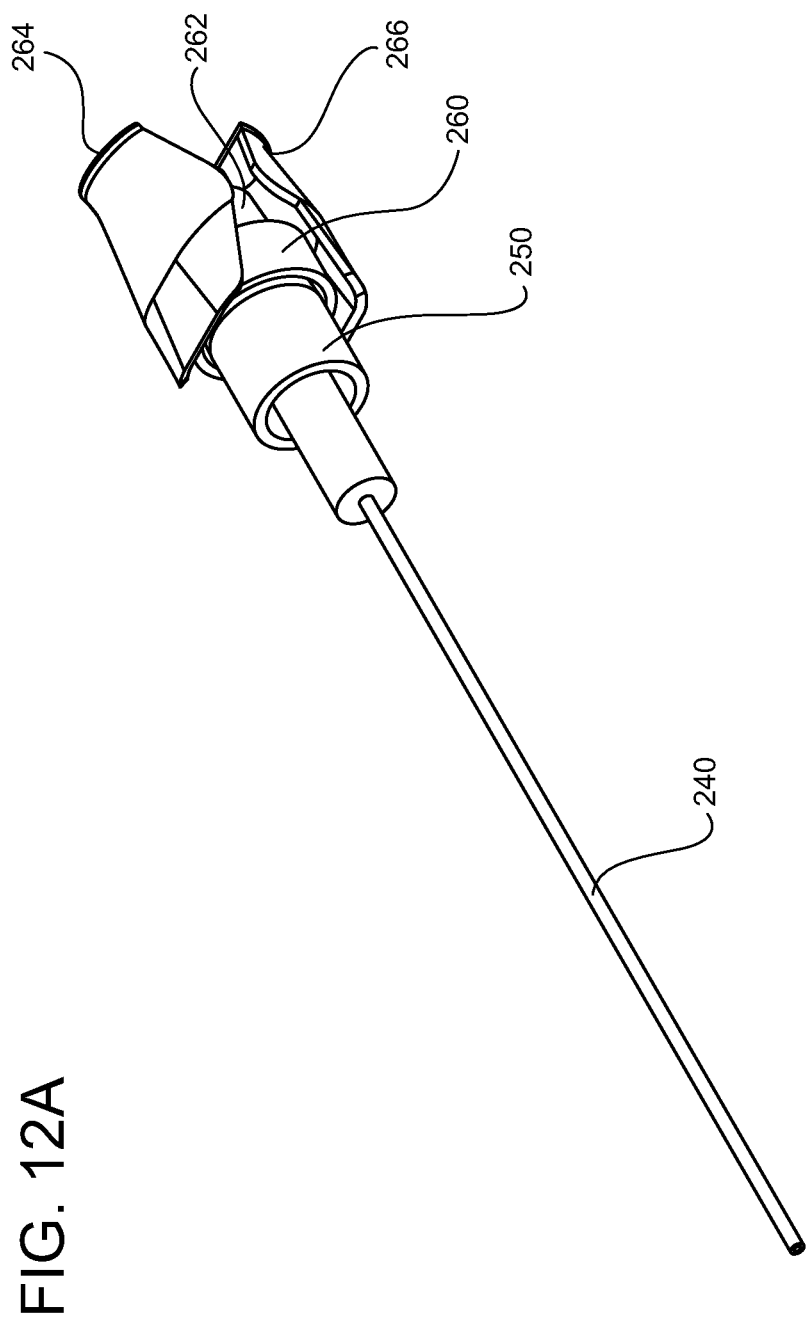

ANTIMICROBIAL IV ACCESS CAP

RELATED APPLICATION

This application claims priority to U.S. Provisional Patent Application No. 61/364,447, entitled ANTIMICROBIAL I.V. ACCESS CAP, filed on Jul. 15, 2010, which is incorporated herein in its entirety.

BACKGROUND OF THE INVENTION

The present invention relates generally to systems and method for preventing contamination of access ports. In particular, this disclosure discusses an antimicrobial access cap which is configured to receiving an access port of an intravascular device, an inner surface of the antimicrobial access cap having been treated with an antimicrobial agent.

In the fields of medicine and health care, a patient's skin may be punctured in a variety of manners and for a variety of reasons. In one example, a cannula or an intravenous ("IV") catheter is forced through the patient's skin into an interior space, such as the patient's vasculature. In this example, the cannula or IV catheter can be used for infusing fluid (e.g., saline solution, medicaments, and/or total parenteral nutrition) into the patient, withdrawing fluids (e.g., blood) from the patient, and/or monitoring various parameters of the patient's vascular system. The cannula or IV catheter generally comprises a distal end which is positioned within the patient's vasculature, and a proximal end which is located external to the vasculature of the patient. As such, a physician may access the vasculature of the patient via the exposed, proximal end of the IV catheter.

While an IV catheter is convenient for providing prolonged access to the vasculature of the patient, the exposed portions of the catheter are susceptible to contamination by various strains of bacteria and viruses. Indeed, it is estimated that each year hundreds of thousands of patients in the United States alone develop some form of bloodstream infection that is caused by pathogens that were communicated to the patient through or because of an IV catheter or another IV access device, such as a hypodermic needle. Many of the bacterial pathogens that cause these catheter-related bloodstream infections are introduced into the vasculature of the patient through repeated attempts to access the patient's vasculature via the exposed portion of the IV catheter. Bacterial colonies which develop on the exposed portion of the IV catheter are transferred to the patient by way of a needle or syringe which is inserted into the proximal, exposed portion of the IV catheter.

Often, these catheter-related bloodstream infections cause patient illness and, in some cases, death. Furthermore, because some infections are caused by bacterial strains (e.g., Methicillin-resistant *Staphylococcus aureus* ("MRSA") and Vancomycin-resistant *Enterococci* ("VRE")) that are resistant to antibiotics, such infections can be hard to treat and may be becoming more prevalent. Additionally, because patients that have a bloodstream infection may require additional medical treatment, catheter-related bloodstream infections may also be associated with increased medical costs.

In an attempt to limit bloodstream infections (i.e., catheter-related infections) in hospital, outpatient, home care, and other health care settings, many have implemented sanitary techniques. For example, many health care providers have placed a strong emphasis on wearing gloves, cleaning hands, and cleaning the exposed portion of the IV catheter before inserting a needle or syringe. Some health care providers have devised a medical device cap which includes a cleaning solution, as taught in U.S. patent application Ser. No. 12/877,519, which is incorporated herein by reference, in its entirety. However, the demands of some medical emergency situations often preclude the use of currently available sanitary techniques.

Thus, while methods and systems currently exist to reduce bloodstream infections, challenges still exist. Accordingly, it would be an improvement in the art to augment or even replace current techniques with other techniques.

BRIEF SUMMARY OF THE INVENTION

The systems and methods of the present disclosure have been developed in response to problems and needs in the art that have not yet been fully resolved by currently available infusion systems and methods. Thus, these systems and methods are developed to provide for safer and more efficient rapid infusion procedures.

In some implementations of the present invention, a device is provided for preventing contamination of an access port, the device including an access cap having an inner surface defining a space for receiving a portion of the access port, the inner surface further including an antimicrobial agent. In some implementations, the access port is a portion of an intravenous or intravascular device, such as a y-port. In other implementations, the access port is a male or female luer of an intravascular device. Further still, in some aspects of the present invention the access port is at least one of a syringe, a catheter, a catheter hub, a needle, a piece of intravenous tubing, and/or an input or output valve of a medical device, such as centrifuge or a dialysis machine.

In some aspects of the invention, an access cap is provided which is configured to cover and thereby protect an exposed portion of the access port, thereby preventing contamination of the access port by bacteria or viruses. In some implementations, an access cap is provided which is connected to a portion of the access port. For example, in some implementations access cap is connected or attached to the access port via a tether. In other implementations, access cap is attached to the access port via a hinged tether. Further, in other implementations the access cap is slidably coupled to the intravascular device. Further still, in some implementations the access cap is pivotally coupled at least one of the access port and the intravascular device.

The antimicrobial agent is generally provided on a surface of the access cap such that when the access cap is placed onto the access port, the antimicrobial agent is in direct contact with an exposed portion of the access port. In some implementations, the antimicrobial agent is applied directly to the access cap. In other embodiments, the antimicrobial agent is applied to a material (such as a sponge, a foam, or a gel) which is applied to a surface of the access cap. Thus, when the access cap is placed adjacent to the access port, the antimicrobial agent maintains contact with an exposed or external portion of the access port.

In some implementation of the present invention, a method for preventing contamination of an access port is provided. Some aspects of the invention provide steps for providing a cap having an inner surface defining a space for receiving a portion of the access port, applying an antimicrobial agent to a portion of the inner surface, and attaching the cap to the access port. In some implementations, the access port is an intravenous or intravascular device. In other implementations, a further step is provided wherein the antimicrobial agent is retained by a material disposed within the inner surface of the cap.

Further still, in some implementations of the present invention an access port adapter, or an intravenous device adapter is provided having a body which includes a proximal end and a distal end, the proximal end having a first coupling surface for receiving a first or upstream intravascular device, and the distal end having a second coupling surface for receiving a second or downstream intravascular device. The access port adapter further includes a cap or access cap coupled to the body of the access port adapter, the cap having an inner surface defining a space for receiving a portion of the access port, and an antimicrobial agent disposed within the inner surface of the cap.

In some aspects of the present invention, the first and second coupling surfaces are threaded. In other aspects of the invention, a material is disposed within the inner surface of the cap which is capable of receiving and storing an antimicrobial agent. The material generally includes adsorptive or absorptive properties which allow the antimicrobial agent to be stored within the material. In some implementations, the material includes at least one of a sponge, a gel, a foam material, a woven material, a non-woven material, and a polymeric material.

The present invention further includes methods for manufacturing an antimicrobial IV access cap, wherein the method includes steps for coupling an access cap to a portion of an intravenous device, the intravenous device having an access port, and inserting an antimicrobial agent within an inner surface of the access cap, the inner surface of the access cap being configured to receive an exposed portion of the access port. The method for manufacturing the antimicrobial IV access cap further includes steps for hingedly coupling the access cap to a body portion of the intravenous device, as well as modifying the tethered connection between the access cap and the intravenous device with various other features, discussed in detail below.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

FIG. 5 is a plane view of an intravenous device adapter and antimicrobial access cap in accordance with a representative embodiment of the present invention.

FIG. 6 is a plane view of an intravenous device adapter and antimicrobial access cap in accordance with a representative embodiment of the present invention.

FIG. 8, as shown in parts A and B, is a plane view of an intravenous device adapter and antimicrobial access cap in accordance with a representative embodiment of the present invention.

FIG. 9, as shown in parts A and B, is a plane view of an intravenous device adapter and antimicrobial access cap in accordance with a representative embodiment of the present invention.

DETAILED DESCRIPTION OF THE INVENTION

Embodiments of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Figure 1:
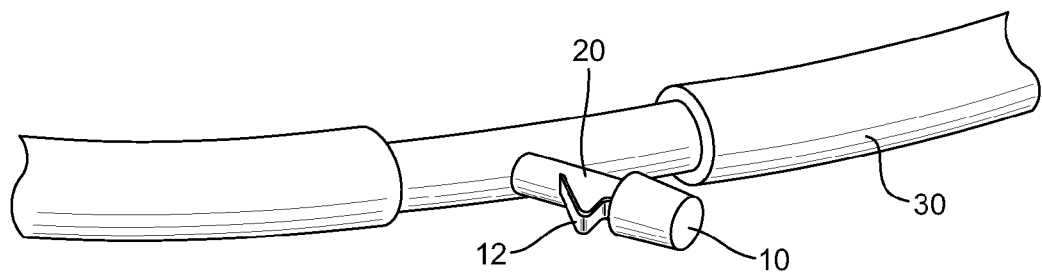
FIG. 1 is a perspective view of an access port in accordance with a representative embodiment of the present invention.

The systems and methods of the present invention are generally designed for use in combination with a vascular infusion system capable delivering an infusant to the vascular system of a patient. Referring now to FIG. 1, an antimicrobial IV access cap 10 is shown, in accordance with a representative embodiment of the present invention. In some embodiments, cap 10 prevents contamination of an access port 20, such as a y-port of an intravenous tube 30. In some embodiments, cap 10 further comprises a tether 12 by which cap 10 is coupled to a portion of access port 20. In this way, cap 10 may be removed from covering access port 20 without being misplaced or lost. In some embodiments, cap 10, tether 12 and access port 20 comprises the same material. In other embodiments, cap 10, tether 12 and access port 20 comprise two or more materials. Further, in some embodiments access port 20 comprises at least one of an intravenous access port, a PRN adapter, a Posiflow access port, a Q-Syte access port, a Maxiplus access port, and a Clearlink access port. Access port 20 may further include any port or other structure which may be utilized to access the vasculature of a patient.

Figure 2:
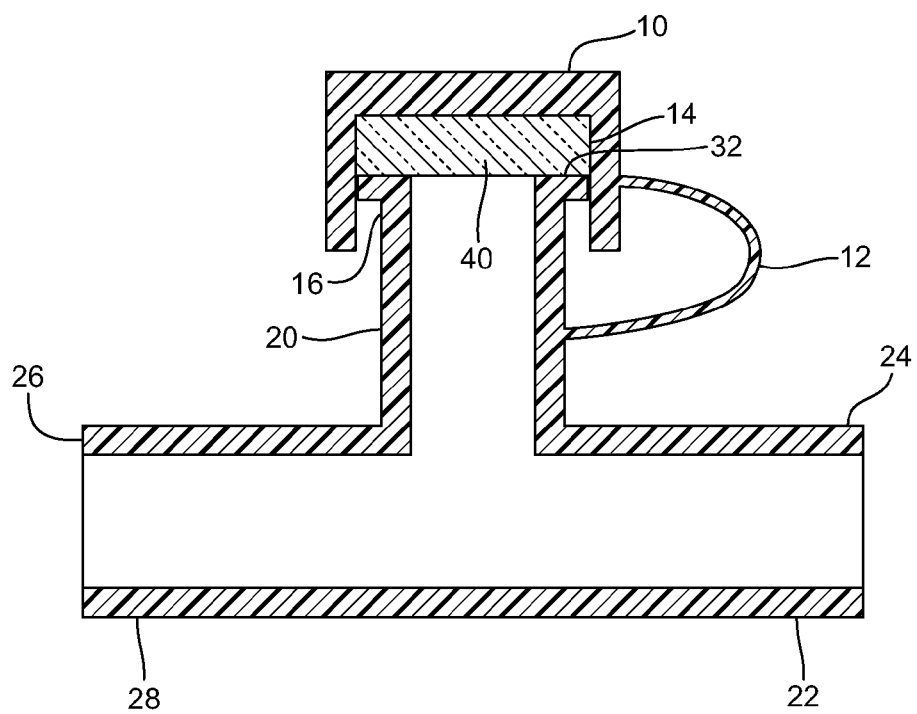
FIG. 2 is a cross-section side view of an access port in accordance with a representative embodiment of the present invention.

Referring now to FIG. 2, a cross-section of an access port 20 and IV access cap 10, is shown. In some embodiments, access port 20 comprises a portion of an intravenous tube 22. In other embodiments, access port 20 comprises a portion of a catheter tubing adapter 28, wherein a first and second end 24 and 26 of the catheter tubing adapter is fitted with a section of intravenous tubing, thereby permitting flow between the sections of intravenous tubing, via adapter 28.

Cap 10 generally comprises an inner surface 14 which defines a space for receiving a portion 16 of access port 20. The inner surface 14 further defines a space for storing an antimicrobial agent 40. In some embodiments, antimicrobial agent 40 comprises a material, solution, compound or coating which prevents colonization of undesirable bacteria and viruses. In some embodiments, antimicrobial agent 40 is selected from the group of chlorhexidine gluconate, chlorhexidine acetate, PCMX, Triclosan, silver sulfadiazine, and the like. In other embodiments, antimicrobial agent 40 comprises a topical antibiotic, such as Mupirocin, bacitracine, and the like.

In some embodiments, antimicrobial agent 40 is applied directly to the inner surface 14 of access cap 10. In other embodiments, antimicrobial agent 40 is retained within the inner surface 14 of access cap 10 via a material, such as a sponge material, a gel material, a foam material, a woven material, a non-woven material, and/or a polymeric material. The antimicrobial agent 40 is applied to the inner surface 14 of cap 10 such that when cap 10 is placed over access port 20, antimicrobial agent 40 contacts an opening surface 32 of access port 20. In this way, antimicrobial agent 40 prevents colonization of bacterial and/or viruses within access port 20.

Figure 3:
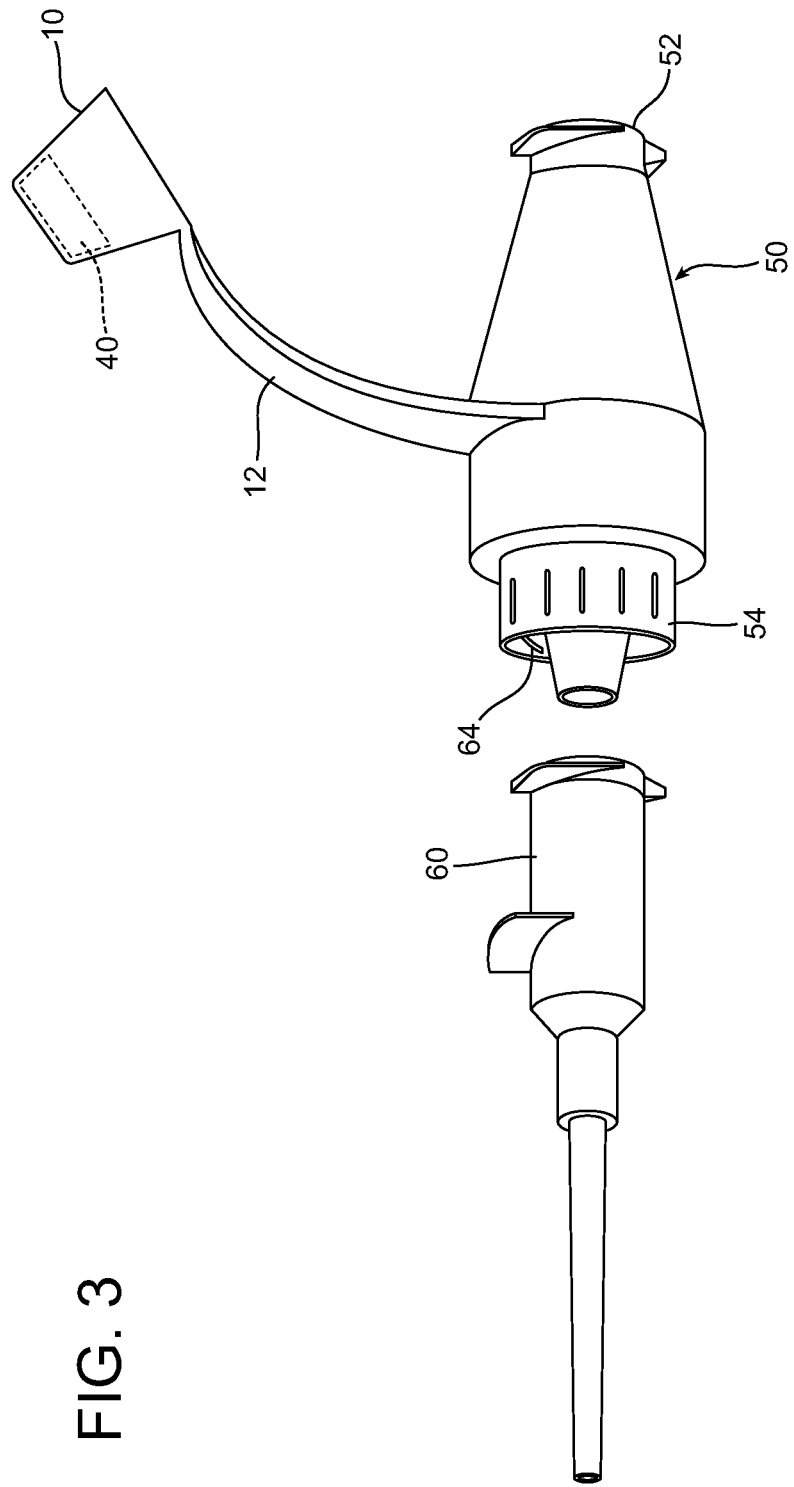
FIG. 3 is a perspective view of an intravenous device adapter and downstream intravenous device in accordance with a representative embodiment of the present invention.

Referring now to FIG. 3, in some embodiments access cap 10 comprises a portion of an intravenous device adapter 50. Adapter 50 generally comprises a proximal end 52 having a first threaded surface 62 for receiving an upstream intravenous device (such as a male luer from a syringe, not shown), and a distal end 54 having a second threaded surface 64 for threadedly receiving a downstream intravenous device 60, such as catheter 60. Adapter 50 thereby permits the addition of an access cap 10 to a downstream intravenous device 60 which otherwise does not include an antimicrobial access cap 10.

Figure 4:
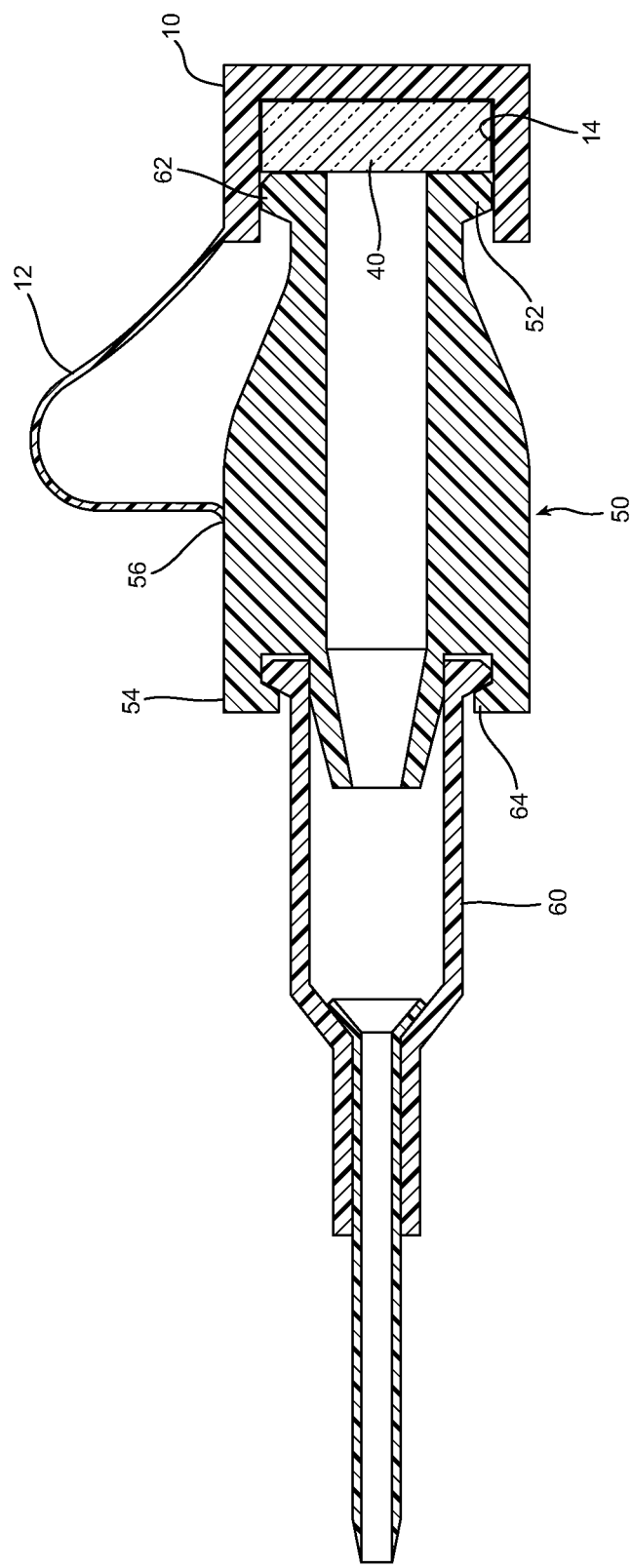
FIG. 4 is a cross-section side view of an intravenous device adapter joined to a downstream intravenous device in accordance with a representative embodiment of the present invention.

Distal end 54 is threadedly coupled to downstream intravenous device 60 via the second threaded surface 64 thereby preventing bacterial colonization between adapter 50 and downstream intravenous device 60, as shown in FIG. 4. When not being used, proximal end 52 is insertedly position within inner surface 14 of access cap 10 such that antimicrobial agent 40 is in direct contact with proximal end 52. When ready for use, access cap 10 is removed from proximal end 52 thereby permitting a threaded connection between threaded surface 62 and an upstream intravenous device (not show).

One having skill in the art will appreciate that the interaction between access cap 10 and intravenous device adapter 50 may be accomplished by any number of different techniques. For example, in some embodiments access cap 10 is tethered to the outer surface 56 of adapter 50, as shown in FIG. 4. However, in some embodiments access cap 10 comprises a tether 70 having a loop 72, defining a distal end of the tether 70, wherein loop 72 is positioned around the second threaded surface 64 of distal end 54, as shown in FIG. 5.

With reference to FIG. 6, in some embodiments access cap 10 further comprises a plurality of threads 18 formed on the inner surface 14 of cap 10 whereby cap 10 may be threadedly coupled to the first threaded surface 62 of proximal end 52. Further, in some embodiments tether 70 further comprises a second loop 74 which defines a proximal end of the tether. The second loop 74 is secured in a groove 32 provided on an outer surface of access cap 10, thereby permitting free rotation of access cap 10 when threadedly coupling access cap 10 proximal end 52 of adapter 50.

Figure 7A:
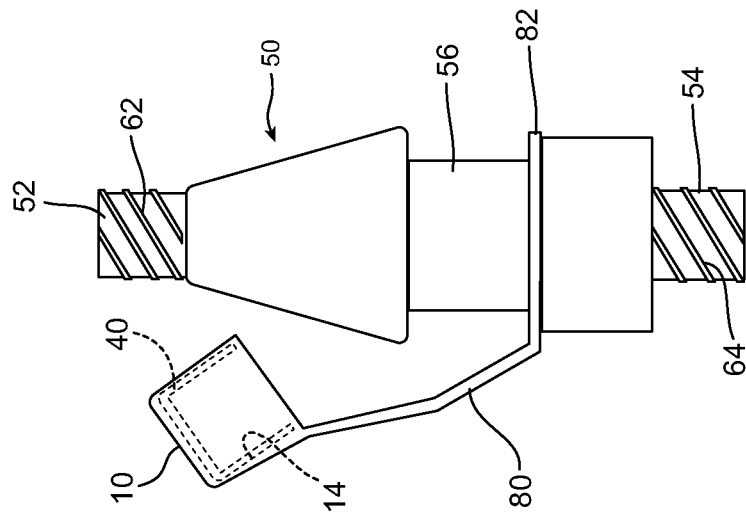
FIG. 7, as shown in parts A-E, is a plane view of an intravenous device adapter and antimicrobial access cap in accordance with a representative embodiment of the present invention.
Figure 7B:
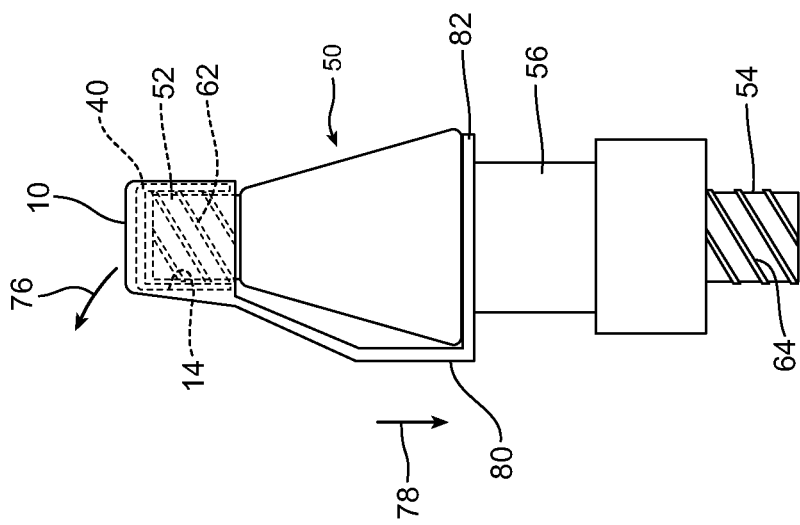

In some embodiments, tether 80 comprises a loop 82 configured to ride within a channel 56 formed on an outer surface of adapter 50, as shown in FIGS. 7A-7E. Referring now to FIG. 7A, in some embodiments access cap 10 is removed from proximal end 52 by first moving access cap 10 in an upward-backward direction 76. Once access cap 10 has cleared proximal end 52, access cap and tether 80 are moved in a downward direction 78, thereby fully exposing proximal end 52, as shown in FIG. 7B. Proximal end 52 is recapped by reversing the movements by which access cap 10 was removed from proximal end 52.

Figure 7E:
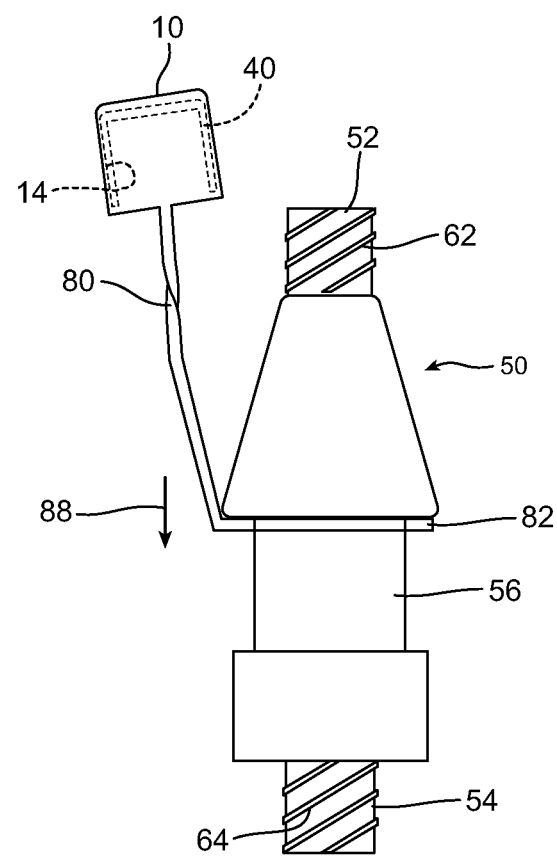

In some embodiments, tether 80 further comprises a lever 84 whereby the user by shift tether 80 in a proximal direction 86 with one hand, thereby advancing access cap 10 in a proximal direction which results in access cap 10 being removed from proximal end 52, as shown in FIGS. 7C and 7D. In some embodiments, access cap 10 is biased away from intravenous device adapter 50 due to outwardly biased tension provided in tether 80. Thus, when access cap 10 is advanced beyond proximal end 52, access cap 10 automatically springs away from proximal end 52 thereby providing unobstructed access to proximal end 52. Access cap is reapplied to proximal end 52 by forcing access cap 10 towards adapter 50 until the cap opening is aligned with proximal end 52. Access cap 10 is then slid in a distal direction onto the proximal end 52 thereby causing loop 82 of tether 80 to resume its initial position within channel 56 of adapter 50. In some embodiments, access cap 10 is twisted by the user such that no portion of cap 10 overlaps adapter 50, as shown in FIG. 7E. Access cap 10 and tether 80 are then slid in a distal direction 88 to resume the initial position of loop 82 within channel 56 of adapter 50.

In some embodiments, intravenous device adapter 50 further comprises a hinged antimicrobial cap 100, as shown in FIGS. 8A and 8B. Access cap 100 may comprise a different design than access cap 10. For example, in some embodiments access cap 100 comprises a platform 102 having a surface 104 against which the antimicrobial agent 40 is applied. In some embodiments, platform 102 further comprises a lever 110 or handle whereby access cap 100 is manipulated by the user, with one hand, to remove access cap 100 and antimicrobial agent 40 from proximal end 52 of adapter 50.

In some embodiments, access cap 100 is hingedly coupled to adapter 50 via a hinged tether 120. Hinged tether 120 includes a hinged joint 122 which moves access cap 100 between a closed position (as shown in FIG. 8A) and an opened position (as shown in FIG. 8B). In some embodiments, hinged joint 122 biases access cap 100 against proximal end 52 when in the closed position. In other embodiments, hinged joint 122 biases access cap 100 away from proximal end 52 when in the opened position. Thus, the user may move access cap 100 between the opened and closed positions as desired to access the vasculature of a patient.

Referring now to FIGS. 9A and 9B, in some embodiments tether 130 comprises a loop 132 defining a distal end of the tether, and a hinged joint 140 coupled to the platform 102 of hinged cap 100, which defines the proximal end of tether 130. Loop 132 is generally configured to ride in groove or channel 56 of adapter 50 between proximal and distal positions. When in a proximal position (as shown in FIG. 9A), access cap 100 is in a closed position such that antimicrobial agent 40 is in contact with proximal end 52 of adapter 50. Tether 130 further comprises a lever 134 or handle by which the user may, with one hand, move tether 130 between the proximal and distal positions. When moved to a distal position (as shown in FIG. 9B), access cap 100 is moved to an opened position such that access cap 100 is cleared from proximal end 52. In some embodiments, the access cap 100 is automatically moved from the closed position to the opened position as a result of the user sliding tether 130 in a distal direction. In other embodiments, the user first flips access cap 100 to an opened position and then slides tether 130 to the distal position.

Figure 10A:
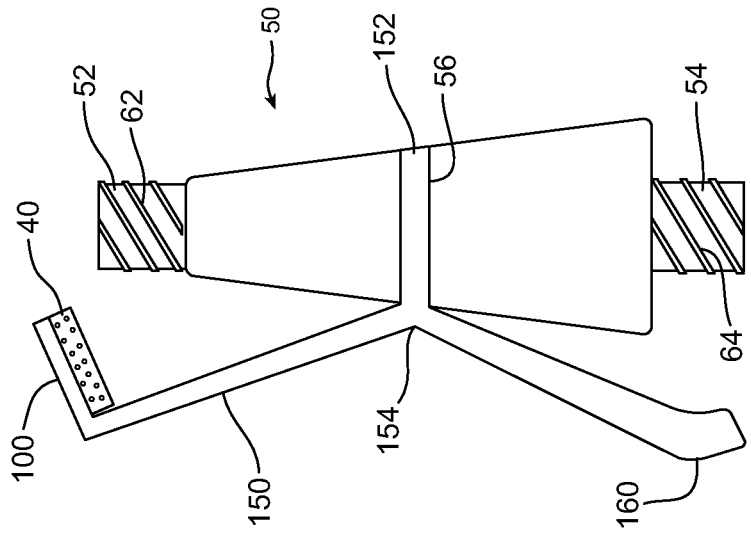
FIG. 10, as shown in parts A and B, is a plane view of an intravenous device adapter and antimicrobial access cap in accordance with a representative embodiment of the present invention.
Figure 10B:
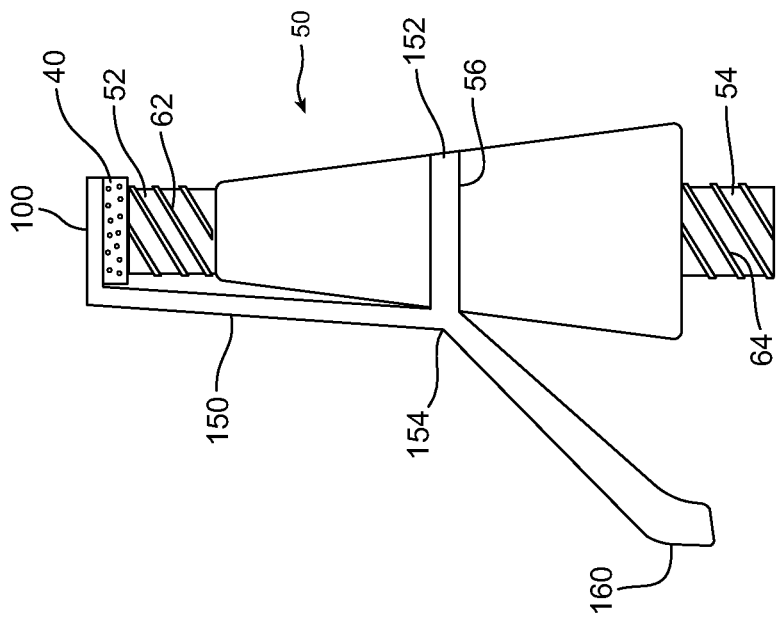

In some embodiments, tether 150 comprises a loop 152 which defines a middle portion of tether 150, as shown in FIGS. 10A and 10B. Loop 152 is generally configured to sit within a groove or channel 56 of adapter 50 which maintains the position at which tether 150 is attached to adapter 50. In some embodiments, the interaction between loop 152 and channel 56 provides a pivot point or fulcrum 154 for tether 150. Thus, when the lever portion 160 of tether 150 is pushed inwardly towards the distal end 54 of adapter 50, tether 150 pivots about fulcrum 154 thereby causing access cap 100 to be removed from proximal end 52 in an outward direction, as shown in FIG. 10B. When lever portion 160 is released, access cap 100 is returned to its initial position which results in antimicrobial agent 40 contacting proximal end 52, as shown in FIG. 10A.

Figure 11A:
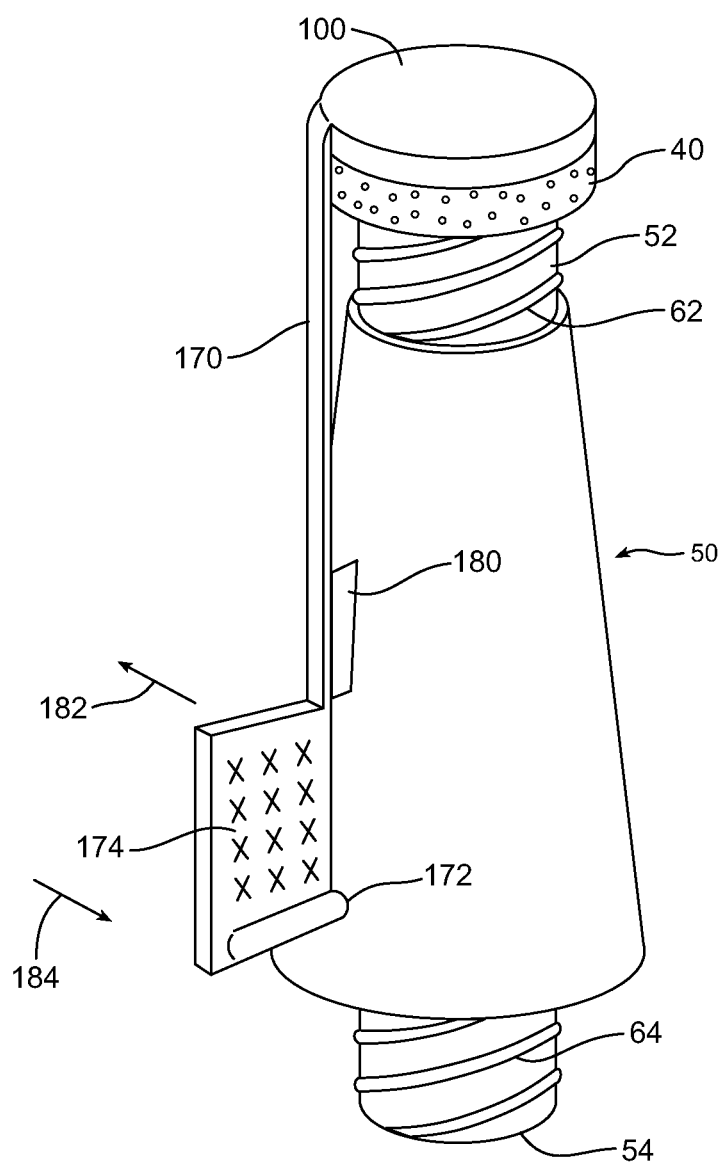
FIG. 11, as shown in parts A and B, is a plane view of an intravenous device adapter and antimicrobial access cap in accordance with a representative embodiment of the present invention.
Figure 11B:
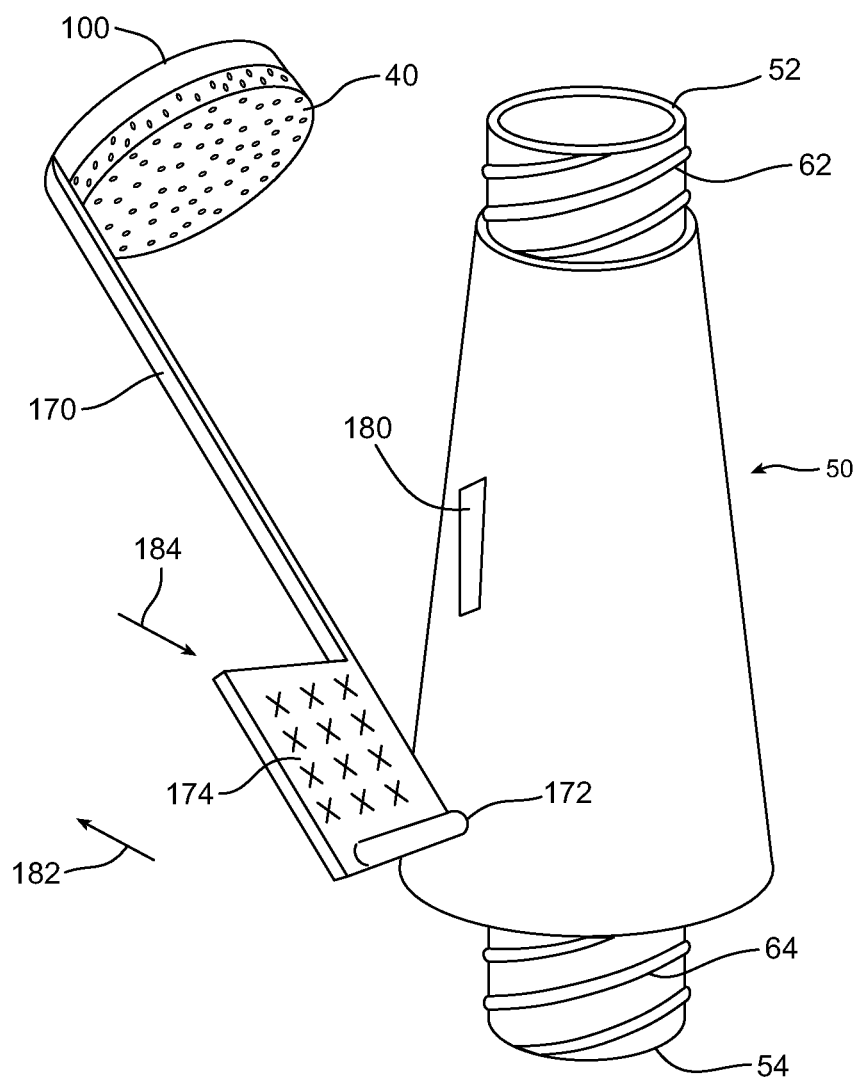

Referring now to FIGS. 11A and 11B, in some embodiments tether 170 comprises a rigid lever having a proximal end coupled to access cap 100, and a distal end pivotally coupled to intravenous device adapter 50. Tether 170 further comprises a handle or pad 174 to facilitate a user in manipulating a rotated position of tether 170 relative to adapter 50.

The pivoting connection 172 between tether 170 and adapter 50 enables tether 170 to be pivoted or rotated between a closed position (as shown in FIG. 11A) and an opened position (as shown in FIG. 11B). In some embodiments, pivoting connection 172 is spring-loaded, such that tether 170 is biased into the closed position. In some embodiments, adapter 50 further comprises a stop 180 which prevent over-forward rotation of tether 170 when in the closed position.

A user accesses proximal end 52 of adapter 50 by pushing pad 174 in rearward direction 182, thereby causing access cap 100 to be displaced from proximal end 52, as shown in FIG. 11B. Pad 174 is configured such that a user may manipulate the position of access cap 100 with a single hand, thereby freeing the user's other hand to attach an intravenous device to the proximal end 52 of adapter 50. Upon releasing pad 174, access cap 100 automatically rotates in a forward direction 184 thereby returning access cap 100 to its initial position which results in antimicrobial agent 40 resuming contact with proximal end 52, as shown in FIG. 11A.

In some embodiments, a section of intravenous tubing 240 comprises a male luer connector 250. The male luer connector 250 enables access to the intravenous tubing 240. For example, in some embodiments an infusion device, such as a syringe (not shown), is attached to the intravenous tubing 240 via a threaded connection between the male luer connector 250 and the syringe. In some embodiments, an exposed surface of male luer connector 250 is protected with a spring hinge cap 260, as shown in FIGS. 12A-12D. For example, in some embodiments spring hinge cap 260 comprises a set of distal threads thereby enabling spring hinge cap 260 to be threadedly coupled to male luer connector 250. In other embodiments, spring hinge cap 260 is press fit over the outer diameter of the male luer connector housing. Further, in some embodiments spring hinge cap 260 comprises a set of proximal threads 262 thereby enabling spring hinge cap 260 to be threadedly coupled to a syringe or other infusion device.

In other embodiments, spring hinge cap 260 is fitted over male luer connector 250 such that the proximal threaded surface of male luer connector 250 passes through a body portion of cap 260 and is positioned inside cap 260. As such, male luer connector 250 may still be accessed by manipulating cap 260 to reveal the proximal threaded surface of male luer connector 250.

Figure 12B:
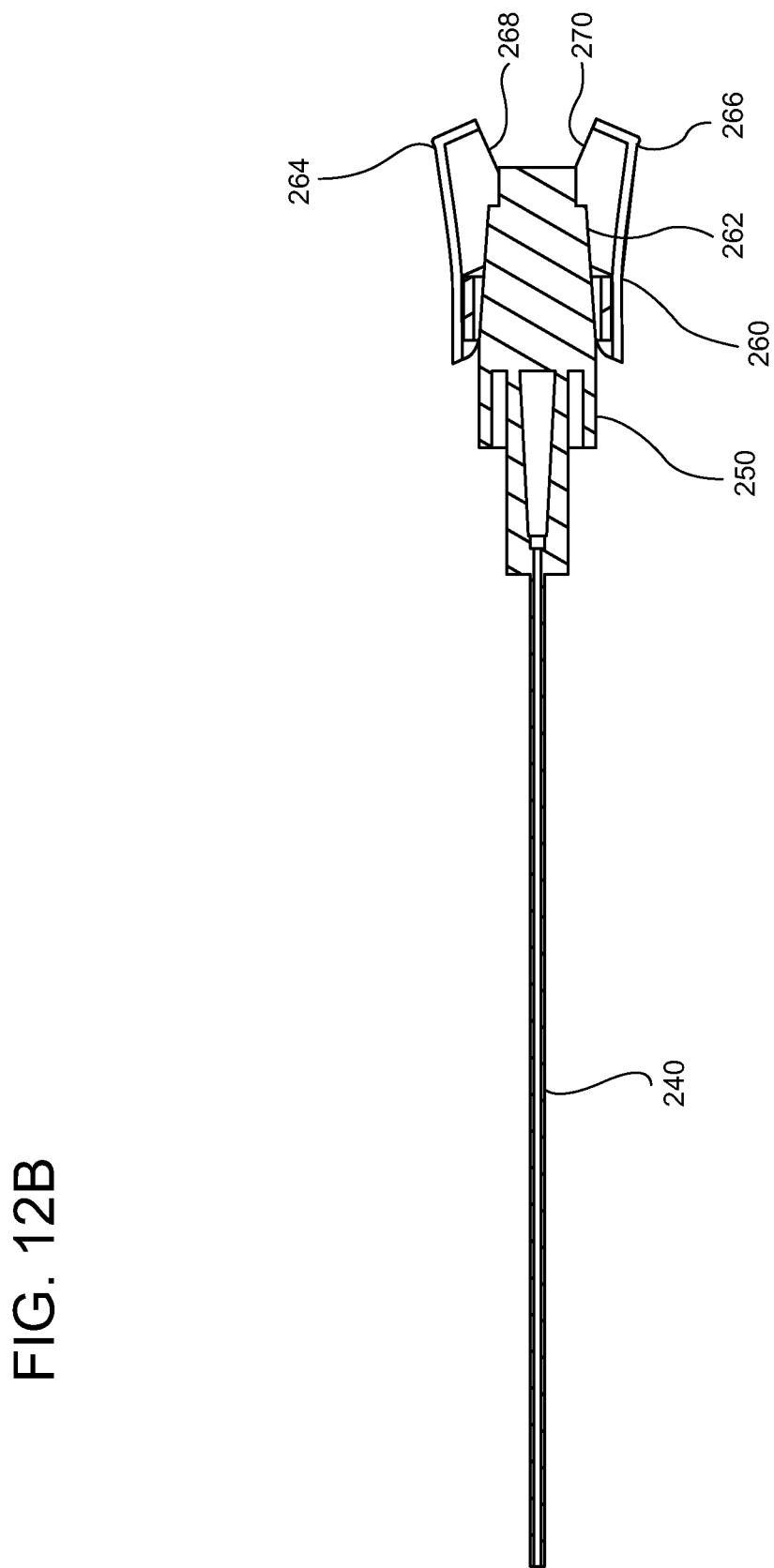
FIG. 12, as shown in parts A-D, provides various views of an intravenous device and antimicrobial spring hinge cap in accordance with a representative embodiment of the present invention.
Figure 12C:
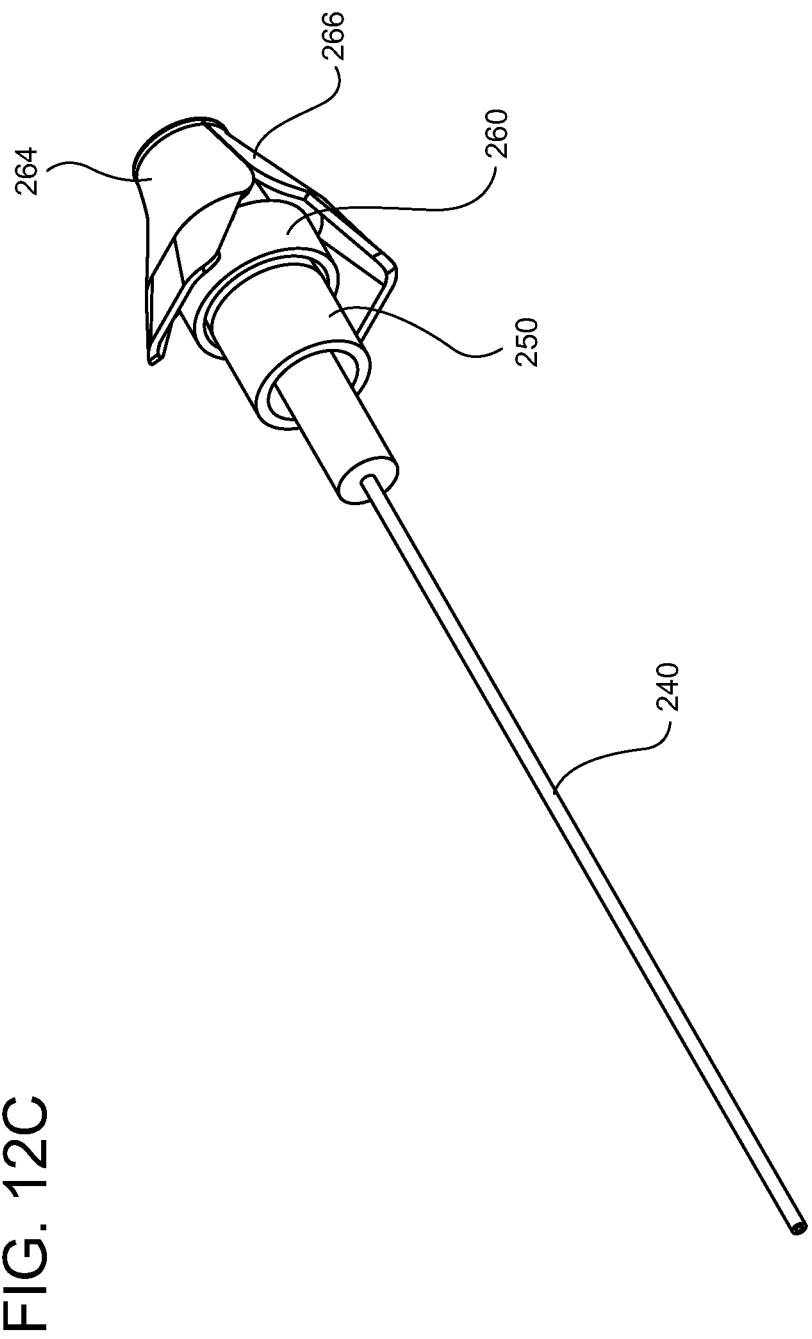
Figure 12D:
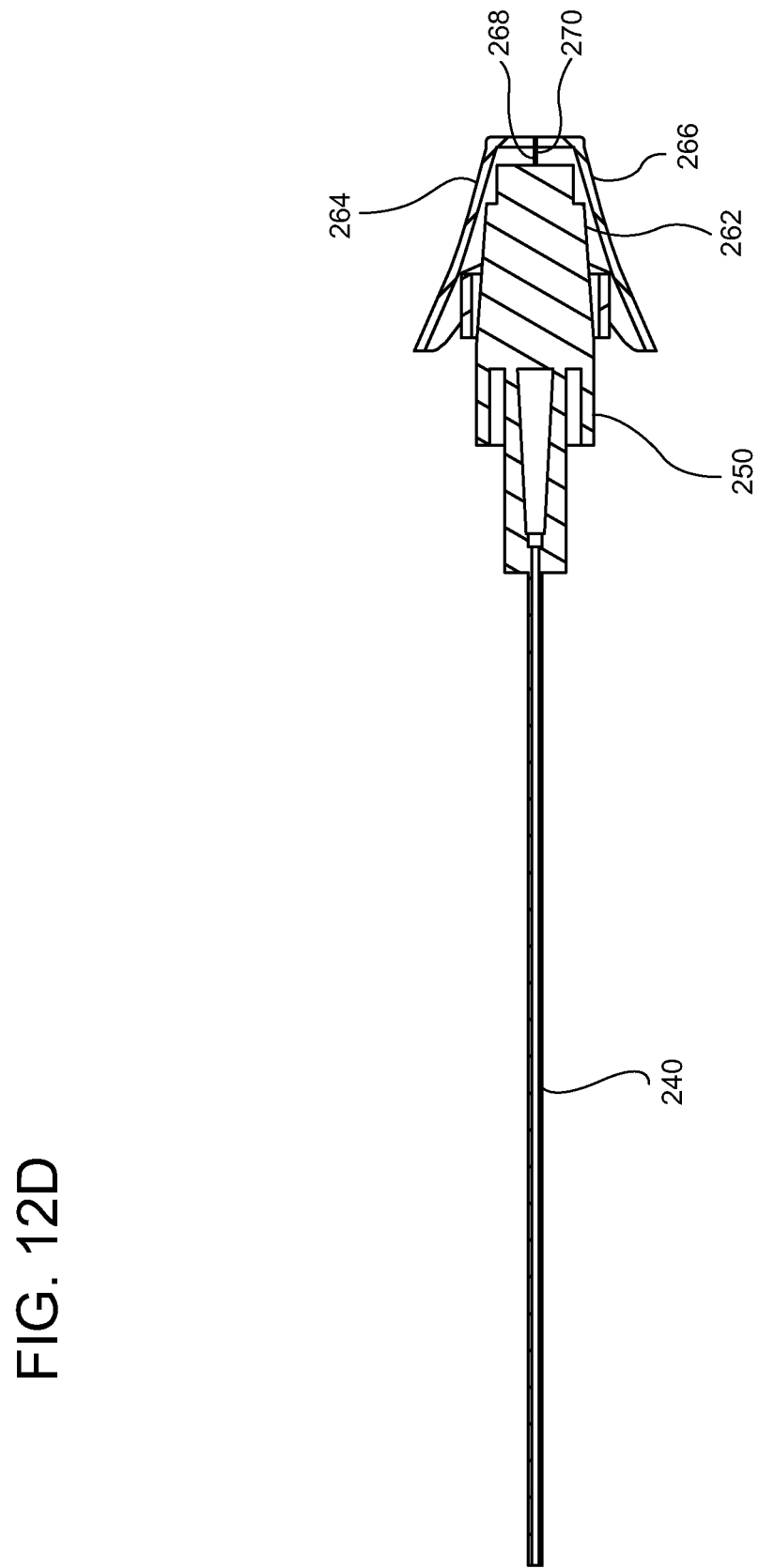

In some embodiments, spring hinge cap 260 comprises a first tab 264 and a second tab 266, each of which is hingedly coupled to a body portion of spring hinge cap 260. In some embodiments, first and second tabs 264 and 266 are further pivotally coupled to a body portion of cap 260 thereby enabling an opened position, as shown in FIGS. 12A and 12B, and closed position, as shown in FIGS. 12C and 12D. Further, in some embodiments first and second tabs 264 and 266 are spring loaded, such that the tabs 264 and 266 are biased into the closed position, wherein the proximal ends of tabs 264 and 266 are in contact with one another. The tabs 264 and 266 are manually biased into the opened position by squeezing the distal ends of tabs 264 and 266 inwardly towards the body of spring hinge cap 260. In some embodiments, spring hinge cap 260 opens when tabs 264 and 266 are squeezed, thereby exposing the female connection of the luer connector for system connection access.

In some embodiments, tabs 264 and 266 further comprise an inner surface 268 and 270, respectively, which form a seal when in the closed position. In some embodiments, inner surfaces 268 and 270 are coated with an antimicrobial agent, in accordance with the teachings of the present invention. Thus, when in the closed position the exposed proximal surfaces of male luer connector 250, or proximal threads 262 of cap 260, are contained within the antimicrobial agent coating of tabs 264 and 266, thereby preventing undesirable contamination thereof.

Referring now to FIGS. 13A-13D, in some embodiments a cap 280 is provided having a lid 282 which is hingedly coupled to a body portion 290 of cap 280. Body portion 290 generally comprises an internal space for receiving an access port or other intravenous device. In some embodiments, the internal space of body portion 290 comprises a set of threads for threadedly receiving an access port. In other embodiments, the internal space of body portion 290 is simply press fit over the outer diameter of a male luer connector housing.

Figure 13A:
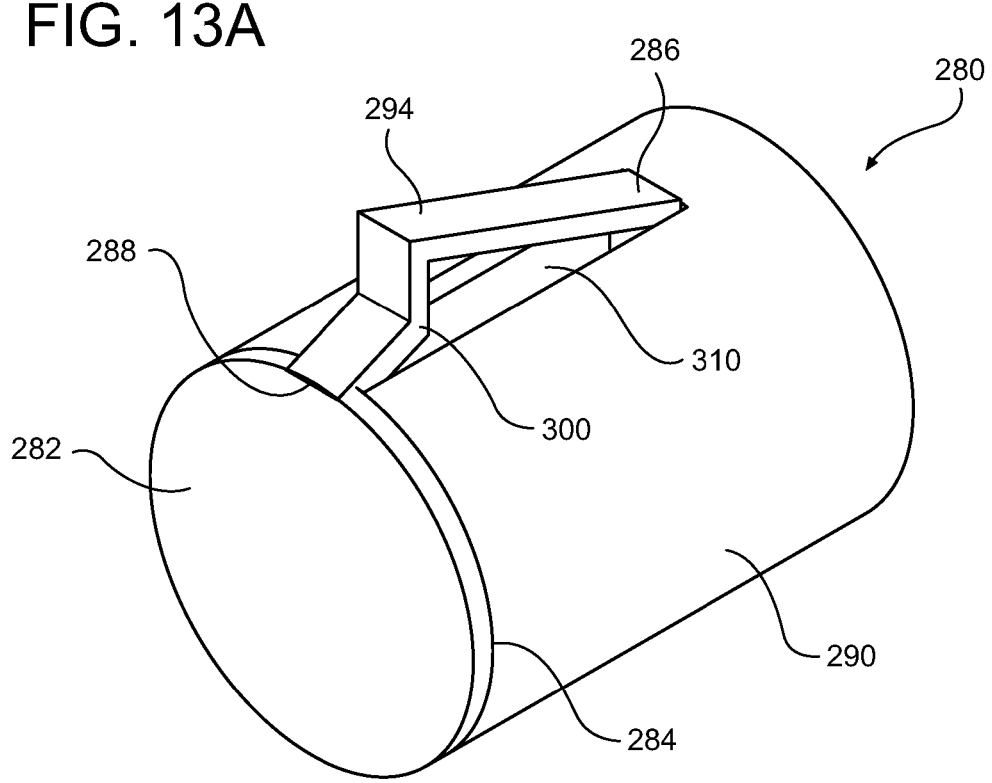
FIG. 13, as shown in parts A-D, provides various views of an antimicrobial access cap in accordance with a representative embodiment of the present invention.
Figure 13B:
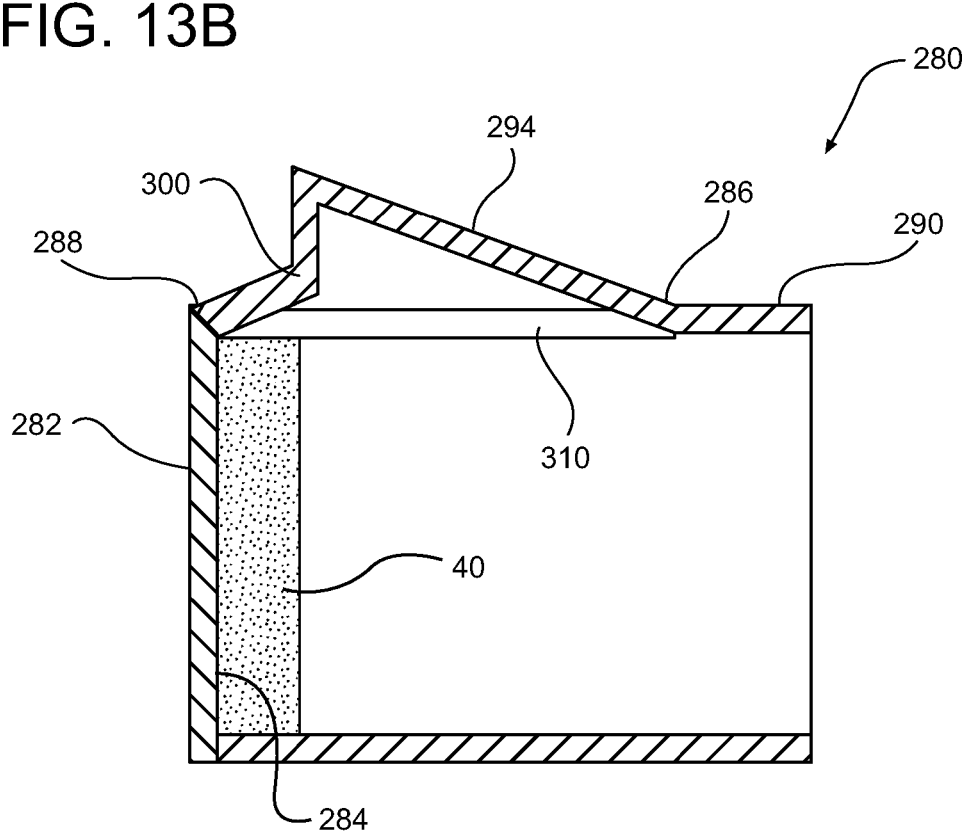

Lid 282 comprises an inner surface 284 which forms a closed end of the internal space when lid 282 is in a closed position, as shown in FIGS. 13A and 13B. In some embodiments, inner surface 284 further comprises an antimicrobial agent 40, in accordance with the teachings of the present invention.

Figure 13C:
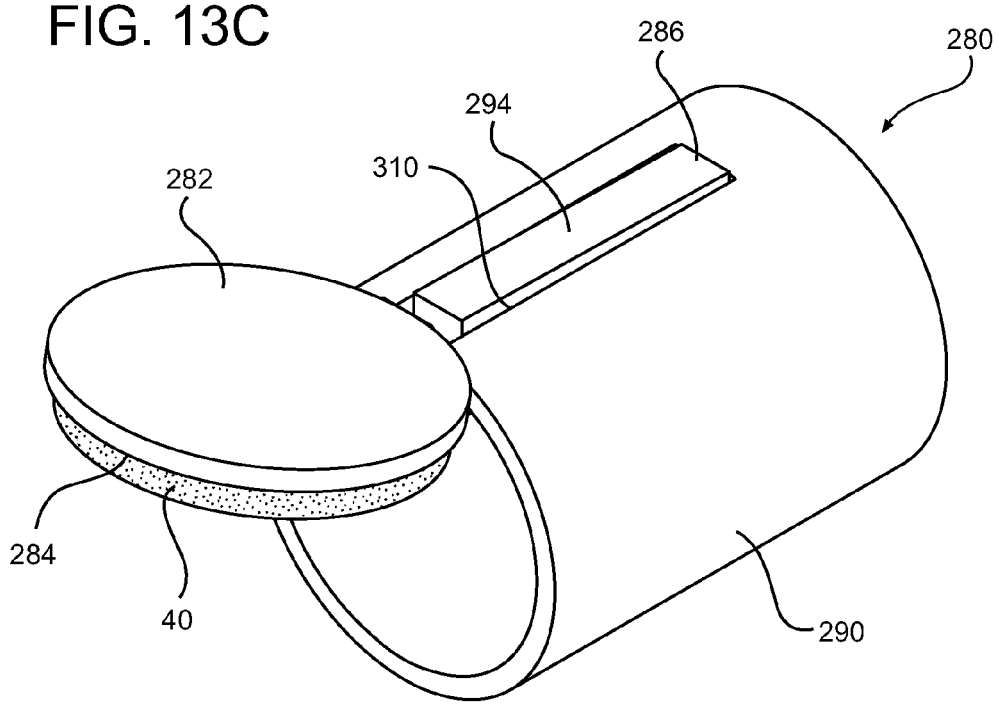
Figure 13D:
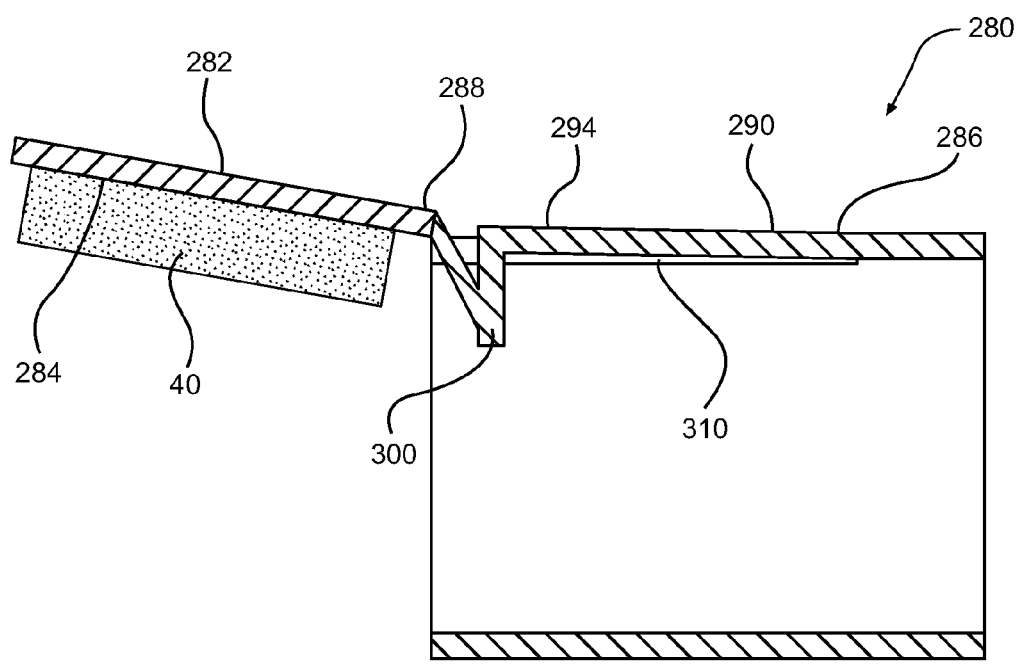

In some embodiments, lid 282 further comprises a lever 294. Lever 294 comprises a first end 286 hingedly coupled to body portion 290, and a second end rigidly coupled to lid 282. Lever 294 further comprises a joint 300 whereby lid 284 and second end 288 pivot into an opened position when lever 294 pressed inwardly towards body portion 290, as shown in FIGS. 13C and 13D. In some embodiments, a channel 310 is provided in body portion 290 thereby enabling lever 294 and joint 300 to be pressed through body portion 290 and into the internal space of body portion 290. Upon releasing lever 294, lid 282 returns to its closed position, as shown in FIGS. 13A and 13B.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. An intravenous device adapter comprising:
a body having a proximal end and a distal end, the proximal end having a first coupling surface for receiving a first intravenous device, and the distal end having a second coupling surface for receiving a second intravenous device, the body further including a channel having a proximal end and a distal end;
a cap having an inner surface configured to contact-the proximal end of the body;
a tether connecting the cap to the body, the tether having a loop at a distal end, the loop extending around the channel to secure the tether to the body, the loop having a width that is less than a width of the channel such that the loop is slidable within the channel between the proximal end and the distal end of the channel, wherein the tether has a length such that, when the loop is at the proximal end of the channel, the cap can be coupled to or removed from the proximal end of the body, and when the loop is at the distal end of the channel, the cap, when not coupled to the proximal end of the body, cannot be coupled to the proximal end of the body or, when coupled to the proximal end of the body, cannot be removed from the proximal end of the body; and
an antimicrobial agent disposed within the inner surface of the cap.

2. The intravenous device adapter of claim 1, wherein the first coupling surface is a threaded surface.

3. The intravenous device adapter of claim 1, wherein the inner surface comprises a threaded surface for threading the cap onto the proximal end of the body.

4. The intravenous device adapter of claim 1, wherein the antimicrobial agent is contained within a material that comprises at least one of a sponge, a gel, a foam material, a woven material, a non-woven material, and a polymeric material.

5. The intravenous device adapter of claim 1, wherein at least one of the first and second intravenous devices is an intravenous catheter.

6. The intravenous device adapter of claim 1, wherein at least one of the first and second intravenous devices is a syringe.

7. The intravenous device adapter of claim 1, wherein the tether includes a lever.

8. The intravenous device adapter of claim 7, wherein the lever extends distally from the loop.

9. The intravenous device adapter of claim 1, wherein the tether includes a hinged joint, and wherein sliding the loop from the proximal end of the channel to the distal end of the channel causes the hinged joint to open thereby removing the cap from the proximal end of the body.

10. An intravenous device adapter comprising:
a proximal end having a first surface for receiving an upstream intravenous device;
a distal end having a second surface for receiving a downstream intravenous device;
a channel formed between the proximal and distal ends;
a cap having an inner surface that contains an antimicrobial agent, the inner surface conforming to the proximal end to allow the cap to be placed over the proximal end; and
a tether that connects the cap to the intravenous device adapter, the tether having a loop that secures the tether within the channel and a proximal end that secures the cap to the tether, the loop having a width that is less than a width of the channel such that the loop is slidable within the channel between a proximal end and a distal end of the channel, wherein the tether has a length such that, when the loop is at the proximal end of the channel, the cap can be coupled to or removed from the proximal end of the adapter, and when the loop is at the distal end of the channel, the cap, when not coupled to the proximal end of the adapter, cannot be coupled to the proximal end of the adapter or, when coupled to the proximal end of the adapter, cannot be removed from the proximal end of the adapter, the proximal end of the channel having a first diameter, the distal end of the channel having a second diameter, a portion of the channel between the proximal and distal ends of the channel having a third diameter, the third diameter being less than the first diameter and the second diameter.

11. The intravenous device adapter of claim 10, wherein the tether includes a lever.

12. The intravenous device adapter of claim 10, wherein the tether includes a hinged joint, and wherein sliding the loop from the proximal end of the channel to the distal end of the channel causes the hinged joint to open thereby removing the cap from the proximal end of the adapter.

* * * * *